United States Patent [19]

Bronstein et al.

[11] Patent Number: 5,756,770
[45] Date of Patent: May 26, 1998

[54] SYNTHESIS OF STABLE, WATER-SOLUBLE CHEMILUMINESCENT 1,2-DIOXETANES AND INTERMEDIATES THEREFOR

[75] Inventors: Irena Y. Bronstein, Newton; Brooks Edwards, Cambridge, both of Mass.

[73] Assignee: Tropix, Inc., Bedford, Mass.

[21] Appl. No.: 630,635

[22] Filed: Dec. 20, 1990

Related U.S. Application Data

[60] Continuation-in-part of Ser. No. 559,152, Jul. 24, 1990, abandoned, which is a division of Ser. No. 367,772, Jul. 17, 1989, abandoned, which is a continuation-in-part of Ser. No. 140,197, Dec. 31, 1987, abandoned.

[51] Int. Cl.⁶ .................................................... C07F 9/06
[52] U.S. Cl. ............................................ 549/220; 549/221
[58] Field of Search ................................... 549/220, 221

[56] References Cited

U.S. PATENT DOCUMENTS 4,956,477  9/1990  Bronstein et al. ................. 549/221

*Primary Examiner*—Amelia Owens

*Attorney, Agent, or Firm*—Oblon, Spivak, McClelland, Maier & Neustadt, P.C.

[57] ABSTRACT

A novel synthesis of 1,2-dioxetane phosphate alkali metal salts and novel intermediates employed in this synthesis are disclosed. A hydroxyaryl enol ether alkali metal salt having the formula:

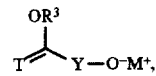

wherein T can be an unsubstituted or substituted adamant-2'-ylidene group, $R^3$ can be a methyl group, Y can be a phenyl group and $M^+$ can be a sodium cation, is reacted with a phosphorohalidate to give the corresponding enol ether ethylene phosphate, which is then reacted with an alkali metal cyanide to give the corresponding enol ether cyanoethyl phosphate diester alkali metal salt intermediate. Singlet oxygen addition to this enol ether cyanoethyl phosphate diester alkali metal salt intermediate to give the corresponding 1,2-dioxetane cyanoethyl phosphate diester alkali metal salt, followed by β-elimination of the cyanoethyl group using an alkali metal hydroxide or the like, gives the corresponding 1,2-dioxetane phosphate alkali metal salt.

3 Claims, No Drawings

SYNTHESIS OF STABLE, WATER-SOLUBLE CHEMILUMINESCENT 1,2-DIOXETANES AND INTERMEDIATES THEREFOR

This application is a continuation-in-part of U.S. patent application Ser. No. 559,152, filed Jul. 24, 1990, which in turn is a division of U.S. patent application Ser. No. 367,772, filed Jul. 17, 1989 (based on PCT application PCT/0589/00016, filed Jan. 3, 1989 in the U.S. Receiving Office based on Japanese patent application No. 185319/88, filed July 25, 1988, and now-abandoned U.S. patent application Ser. No. 140,197, filed Dec. 31, 1987); hence, Ser. No. 367,772 is a continuation-in-part of Ser. No. 140,197 all now abandoned. U.S. patent application Ser. No. 411,387, filed Sep. 22, 1989 now U.S. Pat. No. 4,956,477 as a division of Ser. No. 367,772, and U.S. patent application Ser. No. 537,788, filed Jun. 14, 1990 now U.S. Pat. No. 5,177,241 as a continuation of Ser. No. 411,387, are also included in this chain of copending applications.

BACKGROUND OF THE INVENTION

The above-mentioned copending U.S. patent applications, the entire contents of which are incorporated by reference as though set forth herein, disclose and claim a new synthesis of stable, water-soluble chemiluminescent 1,2-dioxetanes, particularly ones that are enzymatically cleavable, substituted with stabilizing and solubilizing groups and ring-containing fluorophore moieties.

Among the 1,2-dioxetanes that can be obtained by the novel synthetic methods of this and the above-mentioned applications are those represented by the formula:

In this formula the symbol T represents a spiro-bonded stabilizing group, a gem carbon atom of which is also the 3-carbon atom of the dioxetane ring.

Also included among the 1,2-dioxetanes that can be obtained using the novel synthetic methods of this and its above-identified predecessor applications are the 3-(substituted adamant-2'-ylidene)-1,2-dioxetanes described in copending U.S. patent applications Ser. Nos. 574,786 and 574,787, each filed Aug. 30, 1990.

Among the stabilizing groups represented by T are fused, substituted or unsubstituted polycycloalkylidene groups, bonded to the 3-carbon atom of the dioxetane ring through a spiro linkage and having two or more fused rings, each ring having from 3 to 12 carbon atoms, inclusive, e.g. an adamant-2-ylidene group. The fused polycycloalkylidene group may additionally contain unsaturated bonds or 1,2-fused aromatic rings, or X and X' substituents as described hereinbelow.

$OR^3$ is an ether group, preferably a lower alkyl ether group such as a methoxy group, in which the symbol $R^3$ represents a $C_{1-C_{20}}$ unbranched or branched, substituted or unsubstituted, saturated or unsaturated alkyl group, e.g., methyl, ethyl, allyl or isobutyl; a heteroaralkyl or aralkyl (including ethylenically unsaturated aralkyl) group, e.g., benzyl or vinylbenzyl; a polynuclear (fused ring) or heteropolynuclear aralkyl group which may be further substituted, e.g., naphthylmethyl or 2-(benzothiazol-2'-yl) ethyl; a saturated or unsaturated cycloalkyl group, e.g., cyclohexyl or cyclohexenyl; a N, O, or S hetero atom containing group, e.g., 4-hydroxybutyl, methoxyethyl, ethoxyethyl or polyalkyleneoxyalkyl; or an aryl group, any of which may be fused to Y such that the emitting fragment contains a lactone ring, or an enzymatically cleavable group containing a bond cleavable by an enzyme to yield an electron-rich moiety bonded to the dioxetane ring. Preferably, $OR^3$ is a methoxy group.

The symbol Y represents a light-emitting fluorophore-forming group, part of a luminescent substance capable of absorbing energy upon decomposition of the 1,2-dioxetane to form an excited state from which it emits optically detectable energy to return to its ground state. Preferred are phenyl, naphthyl, biphenyl, 9,10-dihydrophenanthryl, anthryl, phenanthryl, pyrenyl and dibenzosuberyl groups, or derivatives thereof. The Y group bonded to the Z and 1,2-dioxetane ring moieties at any of its $sp^2$ carbon atoms can also be a pyridyl, quinolinyl, isoquinolinyl, coumarinyl, carbostyryl or acridinyl group, or derivatives thereof.

The symbol Z preferably represents an enzyme-cleavable group, preferably a phosphate monoester group, containing a bond cleavable by an enzyme to yield an electron-rich moiety bonded to the dioxetane ring, e.g., a bond which, when cleaved, yields a Y-appended oxygen anion.

One or more of the groups represented by the symbols T, $R^3$ and Z can also include a substituent which enhances the water solubility of the 1,2-dioxetane final products, such as a carboxy or carboxy-containing group, e.g., a carboxymethoxy group, a sulfonic acid group, e.g., an aryl sulfonic acid group, a carboxylic acid or sulfonate salt group, or a quaternary amino salt group, e.g., trimethylammonium chloride, with any appropriate counterion.

Enzymatically cleavable 1,2-dioxetanes can be cleaved using an enzyme such as an alkaline phosphatase that will cleave a bond in, for example, a Z substituent such as a phosphate monoester group, to produce a Y oxyanion of lower oxidation potential that will, in turn, destabilize the dioxetane and cleave its ring oxygen-oxygen bond. Alternatively, catalytic antibodies may be used to cleave the Z substituent. Destabilization can also be accomplished using an enzyme such as an oxido-reductase enzyme that will cleave the oxygen-oxygen bond directly.

SUMMARY OF THE INVENTION

It has now been discovered that the 1,2-dioxetanes of formula (I) above and their above-mentioned 3-(substituted adamant-2'-ylidene) analogs can be directly synthesized from enol ether cyanoethyl phosphate diester alkali metal salt intermediates disclosed in the above-identified predecessors of this application, having the formula:

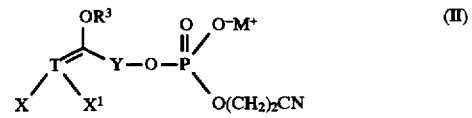

wherein T, Y and $R^3$ are as described hereinabove for formula (I), X and $X^1$ each represent, individually, a substituent, e.g., at the 5' and 7' positions on an adamant-2'-ylidene ring, which can be hydrogen; a hydroxyl group (a slightly electron withdrawing group when hydrogen-bonded to water); a halo substituent, i.e., fluoro or chloro (electron withdrawing groups) or bromo or iodo (polarizable, mesomeric groups); an unsubstituted straight or branched chain lower alkyl group, preferably methyl; a substituted straight or branched chain lower alkyl group, monosubstituted or having two or more substituents which can be the same or different, e.g., a hydroxyalkyl group such as a hydroxymethyl group, a haloalkyl group such as trifluoromethyl, and the like; an unsubstituted aryl group, preferably a phenyl group; a substituted aryl group, preferably one whose aryl ring contains six carbon atoms monosubstituted or having two or more substituents which can be the same or different, e.g., a halo substituent, as in p-bromophenyl or p-chlorophenyl, or an alkoxy substituent, e.g., p-methoxyphenyl (an electron donating group); a hydroxyalkoxy substituent, e.g., hydroxyethoxy or hydroxypropoxy, a cyano group, or an amide group, e.g., a formamido or acetamido group; a carboxylic acid group, or an alkoxy or substituted alkoxy group, e.g., a methoxy group or a 4,5-diphenyloxazol-2-ylmethoxy group; and $M^+$ represents an alkali metal cation, e.g., $Li^+$, $K^+$ or $Na^+$.

The enol ether cyanoethyl phosphate diester alkali metal salts of formula (II) above can be obtained as described in Bronstein, et al. U.S. Pat. No. 4,956,477; see, for example, the reaction scheme at column 7 and column 9, line 49 to column 10, line 10; column 11, line 66 to column 12, line 35 and Example 4.

It has also been discovered that even further advantages can be realized when practicing this invention if the enol ether cyanoethyl phosphate diester alkali metal salt intermediates of formula (II) above are themselves synthesized starting from hydroxyaryl enol ether alkali metal salts prepared as described in Edwards, et al. U.S. patent application Ser. No. 574,789, filed Aug. 30, 1990, now abandoned, using the following reaction sequence:

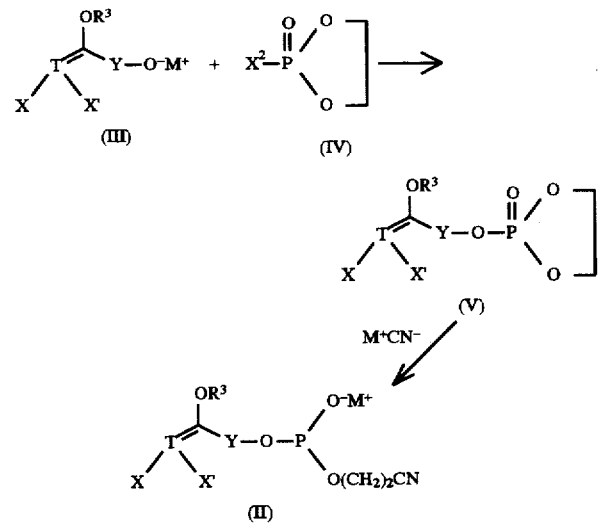

In this reaction sequence T, Y, $R^3$, X, $X^1$ and $M^+$ are as described hereinabove for formulas (I) and (II), and $X^2$ is a halogen, preferably chlorine or bromine.

DETAILED DESCRIPTION OF THE INVENTION

The novel synthetic method of this invention, as indicated above, exhibits its greatest advantages when the first step in the synthesis involves the reaction of a hydroxyaryl enol ether alkali metal salt of formula (III) with a phosphorohalidate of formula (IV), e.g., 2-chloro-2-oxo-1,3,2-dioxaphospholane. This reaction will be carried out in an organic solvent, such as tetrahydrofuran, acetonitrile, dimethyl formamide, dimethyl sulfoxide, or the like, at a temperature of from about room temperature (about 25° C.) to about 35° C. for from about 24 to about 48 hours. Additionally, small quantities of tertiary amines or phase transfer catalysts may be added where appropriate; see Edwards, et al. U.S. patent application Ser. No. 574,789 now abandoned.

Reacting the thus-obtained enol ether ethylene phosphate intermediate (V), following removal of the reaction solvent, with an alkali metal cyanide, e.g., sodium cyanide, in a polar, aprotic solvent, such as dimethylformamide, dimethylacetamide, dimethyl sulfoxide or the like, at a temperature of from about room temperature to about 50° C. for from about 24 to about 72 hours, gives the enol ether cyanoethyl phosphate diester alkali metal salt intermediates (II).

Enol ether cyanoethyl phosphate diester alkali metal salts of formula (II) can be oxidized, either as crude products or after chromatographic purification, using singlet oxygen ($^1O_2$), to give their 1,2-dioxetane counterparts:

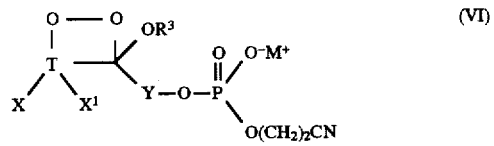

wherein T, Y, $R^3$, X, $X^1$ and $M^+$ are as described hereinabove for formulas (I) and (II).

The conditions used when carrying out this dioxetane ring-forming oxidation reaction can be those described in the literature; see, e.g., Bronstein, et al. U.S. Pat. No. 4,956,477, column 13, lines 29–46 and Examples 5, 6, 8–10, inclusive, 15, 17 and 20. The reaction will preferably be carried out at about 5° C. or below in the presence of methylene blue, tetraphenylporphine, or the like, in a solvent, preferably one that contains a minimum number of hydrogen atoms per carbon atom that will prolong the lifetime of singlet oxygen in the reaction mixture, e.g., a chlorinated aliphatic hydrocarbon such as methylene chloride, chloroform, carbon tetrachloride, or the like, a ketone such as acetone, or the deuterated analogs thereof.

The 1,2-dioxetane cyanoethyl phosphate diester alkali metal salts of formula (VI) above, when reacted in water at a pH of from about 10 to about 13 with slightly more than one equivalent of sodium hydroxide, lithium hydroxide or the like, or a carbonate such as sodium carbonate, potassium carbonate or the like, or in a lower alkanol, such as methanol or ethanol, with slightly more than one equivalent of an alkali metal alkoxide, such as sodium methoxide, sodium ethoxide or the like, or with lithium hydroxide or potassium hydroxide, give the corresponding 1,2-dioxetane phosphate di-alkali metal salts of the formula:

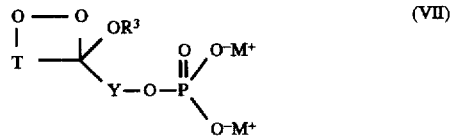

wherein T, Y, $R^3$ and $M^+$ are as described hereinabove for formulas (I) and (II). This reaction can be carried out at temperatures ranging from about 0° C. to about room temperature for from about 15 minutes or less to about 24 hours. A volatile byproduct of this reaction, acrylonitrile, should be removed from the reaction mixture by subjecting it to reduced pressure, e.g., from about 25 to about 2 mm Hg or less, for sufficient time to drive off the acrylonitrile.

Among the advantages realized when practicing this invention which are not found in previous synthetic methods used to prepare 1,2-dioxetane phosphates, particularly when the enol ether cyanoethyl phosphate diester alkali metal salt intermediates of formula (II) above are themselves synthesized starting from the corresponding hydroxyaryl enol ether alkali metal salts, are:

the photooxygenation reaction using singlet oxygen can be carried out more rapidly using higher enol ether concentrations—up to 3–4 times greater than in previous processes—due to the enhanced solubility of the enol ether cyanoethyl phosphate diester alkali metal salt intermediates in chlorinated aliphatic hydrocarbon solvents typically used for this reaction; as a result, throughput is increased without increasing the size of the equipment used.

In order that those skilled in the art can more fully understand this invention, the following examples are set forth. These examples are given solely for purposes of illustration, and should not be considered as expressing limitations unless so set forth in the appended claims. All parts and percentages are weight by volume, unless otherwise indicated.

EXAMPLE I

Sodium 3-(methoxytricyclo[3.3.1.1$^{3,7}$]dec-2-ylidenemethyl)phenoxide (6.07 g, 20.0 mmol) was dissolved in 75 ml of dry tetrahydrofuran in a flask under argon. The resulting brown solution was stirred during the addition of triethylamine (0.87 ml, 6.0 mmol). The flask was then cooled in an ice bath, with vigorous stirring, as 2-chloro-2-oxo-1,3,2-dioxaphospholane (2.29 ml, 24.8 mmol) was added dropwise by syringe. The mixture became slightly cloudy while the color lightened somewhat. The ice bath was removed and the mixture was stirred at room temperature for 27 hours. The solvent was then stripped, with exclusion of moisture to prevent any hydrolysis of the resulting oily, cyclic phosphate triester. An infrared spectrum of the product in dichloromethane was devoid of any absorbances between 3500 and 3300 cm$^{-1}$, and displayed a strong peak at 1300 cm$^{-1}$ (P=O).

The thus-obtained cyclic phosphate was dissolved in 60 ml of dry dimethylformamide to give a slightly cloudy solution. Dry sodium cyanide (1.22 g, 25.0 mmol) was then added under a blanket of argon with stirring. After a reaction period of 48 hours at room temperature, DMF was removed in vacuo (50° C., 1.0 mm Hg) to give a viscous brown oil, which was then dissolved in 75 ml of methanol and filtered to partially remove a finely divided solid. The filtrate was concentrated and again pumped in vacuo for several hours (40° C., 1.0 mm Hg) to further remove DMF. The crude sodium 2-cyanoethyl-3-(methoxytricyclo[3.3.1.1$^{3,7}$]dec-2-ylidenemethyl)phenyl phosphate obtained was triturated twice with 75 ml of ethyl ether and pumped to give a tacky, brown foam weighing 10.3 g. An aqueous sample of the phosphate diester, still occluding some DMF and sodium chloride, was subjected to analytical reverse phase chromatography (Polymer Laboratories PLRP-S polystyrene column using an acetonitrile-water gradient). Under the conditions employed, the enol ether cyanoethyl phosphate diester eluted as the major peak (detection at 270 nm) with a retention time of 10.4 minutes. A sample of the enol ether cyanoethyl phosphate diester prepared as described in U.S. Pat. No. 4,956,477 eluted with the same retention time.

EXAMPLE II

The crude sodium 2-cyanoethyl-3-(methoxytricyclo [3.3.1.1$^{3,7}$]dec-2-ylidenemethyl)phenyl phosphate obtained as described in Example I, supra, was dissolved in 150 ml of chloroform and a saturated solution of methylene blue in chloroform (1.0 ml) was added. This solution was cooled to 0° C., sparged with a flow of oxygen gas and irradiated with a 400 watt, high pressure sodium vapor lamp. The lamp was surrounded with a piece of Kapton polyimide film (DuPont, 5 mil) to filter out unwanted U.V. and blue wavelengths. After 10 minutes another 0.5 ml of the methylene blue solution was added and irradiation was continued for 5 additional minutes. The analytical HPLC chromatogram of an aqueous sample of the photolysate solution revealed the presence of the corresponding 1,2-dioxetane phosphate cyanoethyl diester as a sharp peak, eluting at 10.1 minutes. No enol ether precursor was detected.

The thus-obtained photolysate solution was rotary evaporated (25° C.) to give the crude dioxetane as a green gum, which was immediately dissolved in 30 ml of methanol. Sodium methoxide (4.10 ml of a 4.3 molar solution in methanol) was added dropwise with stirring at room temperature. After a reaction period of 30 minutes, analytical reverse phase HPLC showed that β-elimination of the cyanoethyl group was complete. The light brown, slightly cloudy reaction mixture was concentrated to a paste which was then dissolved in 250 ml of deionized water. This solution, which exhibited a pH of 12.1, was filtered (0.45μ nylon membrane) and subjected to preparative reverse phase HPLC using an acetonitrile-water gradient as described in U.S. Pat. No. 4,931,569. The appropriate eluant fractions were combined and lyophilized to give 6.16 g (72%) of disodium 3-(4-methoxy-spiro(1,2-dioxetane-3,2'-tricyclo [3.3.1.1$^{3,7}$]-decan-4-yl)phenyl phosphate as a fluffy white solid, corresponding to the product obtained in Example 107 of Edwards, et al. U.S. patent application Ser. No. 402,847, filed Sep. 6, 1989 now abandoned.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. Sodium 2-cyanoethyl-3-(4-methoxy-spiro(1,2-dioxetane-3,2'-tricyclo[3.3.1.1$^{3,7}$]decan-4-yl)) phenyl phosphate.

2. A 1,2-dioxetane cyanoethylphosphate diester alkali metal salt represented by the formula:

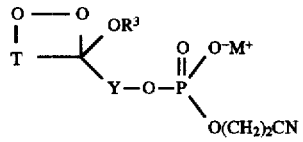

wherein T is an unsubstituted adamant-2'-ylidene group, R$^3$ is methyl, ethyl, benzyl or ethoxyethyl, Y is phenyl or naphthyl and M$^+$ is sodium or lithium.

3. A 1,2-dioxetane cyanoethylphosphate diester alkali metal salt represented by the general formula:

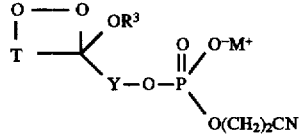

wherein T is an adamant-2'-ylidene group substituted with an alkyl, hydroxyalkyl, halo, alkoxy, cyano, hydroxyl or trifluoromethyl group, R$^3$ is methyl, ethyl, benzyl or ethoxyethyl, Y is phenyl or naphthyl and M$^+$ is sodium or lithium.

* * * * *